United States Patent [19]

Wilkerson

[11] Patent Number: 4,503,065
[45] Date of Patent: Mar. 5, 1985

[54] ANTIINFLAMMATORY 4,5-DIARYL 1-2-HALO IMIDAZOLES

[75] Inventor: Wendell W. Wilkerson, New Castle, Del.

[73] Assignee: E. I. Du Pont de Nemours and Company, Wilmington, Del.

[21] Appl. No.: 404,962

[22] Filed: Aug. 3, 1982

[51] Int. Cl.³ .................. A61K 31/44; A61K 31/415; C07D 401/14; C07D 233/54
[52] U.S. Cl. .................... 514/396; 546/256; 546/278; 548/337; 548/341; 548/346; 514/341; 514/400
[58] Field of Search ................ 548/337; 546/278, 256; 424/273 R, 263

[56] References Cited

U.S. PATENT DOCUMENTS

| | | | |
|---|---|---|---|
| 3,394,105 | 7/1968 | Christie | 528/94 |
| 3,597,343 | 8/1971 | Delzenne et al. | 204/159.23 |
| 3,637,417 | 1/1972 | Green | 427/342 |
| 3,772,441 | 11/1973 | Lombardino | 424/273 R |
| 3,784,691 | 1/1974 | Fitzi et al. | 424/273 R |
| 3,901,908 | 8/1975 | Fitzi et al. | 548/346 |
| 4,182,769 | 1/1980 | Cherkofsky | 424/273 R |
| 4,190,666 | 2/1980 | Cherkofsky | 424/274 |
| 4,199,592 | 4/1980 | Cherkofsky | 424/273 R |
| 4,269,847 | 5/1981 | Niedballa et al. | 424/273 R |
| 4,272,543 | 6/1981 | Niedballa et al. | 424/273 R |

FOREIGN PATENT DOCUMENTS 7124143 7/1971 Japan.

OTHER PUBLICATIONS

*Chem. Abs.* 71:13065r, (1969), [Kocherigin, P. et al., *Khim. Geterotsikl. Soedin.*, 1969, (1), 177–178].
*Chem. Abs.*, 72:90370j, (1970), [Kocherigin, P. et al., *Khim. Geterotsikl. Soedin.*, 1970, (1), 129].
*Chem. Abs.*, 73:120565a, (1970), [Mazur, I. et al., *Khim. Geterotsikl. Soedin.*, 1970, (6), 824–826].
*Chem. Abs.*, 76:25174s, (1972), [Priimenko, B. et al., *Khim. Geterotsikl. Soedin.*, 1971, 7(9), 1248–1251].
*Chem. Abs.*, 76:140642e, (1972), [Priimenko, B. et al., *Khim. Geterotsikl. Soedin.*, 1971, 7(9), 1252–1254].

*Primary Examiner*—Richard A. Schwartz

[57] ABSTRACT

Novel 4,5-diaryl-2-halo imidazoles, for example, 2-bromo-4,5-bis-(4-chorophenyl)imidazole, and their acid addition salts are useful for treating inflammation in mammals. Some of the compounds are also useful as analgesics.

7 Claims, No Drawings

ANTIINFLAMMATORY 4,5-DIARYL 1-2-HALO IMIDAZOLES

BACKGROUND OF THE INVENTION

This invention relates to imidazole derivatives, pharmaceutical compositions containing them and methods of using them to treat inflammation in mammals. More particularly, this invention relates to antiinflammatory 4,5-diaryl-b 2-haloimidazoles.

A few such compounds are known in the art or have been broadly disclosed, but not as analgesics or antiinflammatory agents.

There is a continuing need for safe and effective anti-inflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adrenocortical steroids produce gastric irritation and suppression of normal adrenal function.

The present invention results from efforts to develop new antiarthritic compounds with good antiinflammatory activity and minimal side effects that could be more effective in treating arthritis than presently available drugs.

In addition to antiinflammatory properties, some compounds of this invention are also active as analgesics. This additional property is desirable in treatment of arthritis or related diseases; however, such compounds can be employed solely to alleviate pain.

SUMMARY OF THE INVENTION

It has now been found that compounds of Formula I are useful for treating inflammation in mammals.

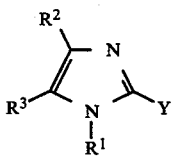

(I)

where
$R^1$ is H, methyl or 1-ethoxyethyl;
$R^2$ is pyridyl or

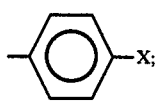

$R^3$ is pyridyl or

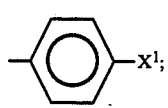

X and $X^1$ are independently F, Cl, Br, $-OR^4$ or $R^4S(O)_n-$;

$R^4$ is methyl or ethyl;
n is 0, 1 or 2; and
Y is F, Cl or Br;
provided that,
(a) when $R^1$ is methyl, then $R^2$ and $R^3$ are both 4-methoxyphenyl; and
(b) when $R^1$ is H, Y is Br and $R^2$ is 4-fluorophenyl, then $R^3$ is other than 4-methoxyphenyl; and
(c) when $R^1$ is H and $R^2$ and $R^3$ are 4-fluorophenyl, then Y is other than Cl;
and pharmaceutically suitable acid addition salts thereof.

This invention therefore relates to novel compounds of Formula I, to pharmaceutical compositions containing such novel compounds, and to the method of using these novel compounds in treating inflammation in mammals.

Preferred, for reasons of high activity and/or ease of synthesis are those compounds of Formula I and their pharmaceutically acceptable salts where
$R^1$ is H; or, independently, where
Y is Cl or Br; or, independently, where
$R^2$ and $R^3$ are

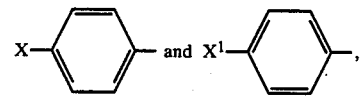

respectively, and where
X and $X^1$ are independently F, Cl, $OCH_3$ or $SCH_3$.

More preferred are those compounds of Formula I and their pharmaceutically acceptable salts where
$R^1$ is H;
Y is Cl or Br; and
$R^2$ and $R^3$ are independently

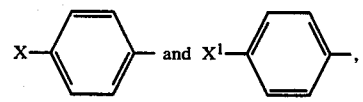

respectively; and
X and $X^1$ are independently F, Cl, $OCH_3$ or $SCH_3$.

Most preferred are 2-bromo-4,5-bis-(4-chlorophenyl)-1H-imidazole and its acid addition salts.

Specifically preferred is 2-bromo-4,5-bis-(4-chlorophenyl)-1H-imidazole, hydrobromide.

Pharmaceutically suitable acid addition salts of the compounds of Formula I are made with physiologically acceptable acids which are known in the art. Such acid salts include hydrochloride, hydrobromide, sulfate, phosphate, nitrate, citrate and maleate.

DETAILED DESCRIPTION OF THE INVENTION

Compounds of Formula I can be prepared by reacting a 4,5-disubstituted imidazole (II) with a source of halogen such as chlorine or bromine in an inert solvent such as carbon tetrachloride, chloroform, methylene chloride, or tetrahydrofuran. Reaction temperatures can range from about 0° to the reflux temperature of the solvent.

Equation 1

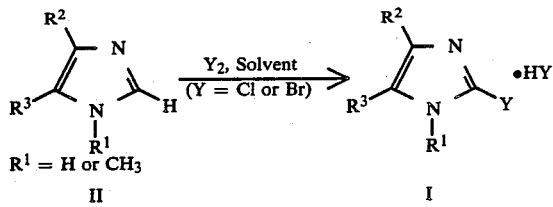

$R^1 = H$ or $CH_3$

Compounds prepared as illustrated in Equation 1 are isolated as the hydrogen halide (HY) salts. Should the free base of Compound I or a different pharmaceutically acceptable salt be required, the HY salt of Compound I can be treated with an appropriate base such as sodium or potassium bicarbonate or triethylamine to obtain the free base. The free base can then be treated with an appropriate acid (HY'), for example hydrochloric or sulfuric acid, to form the HY' salt of Compound I.

Equation 2

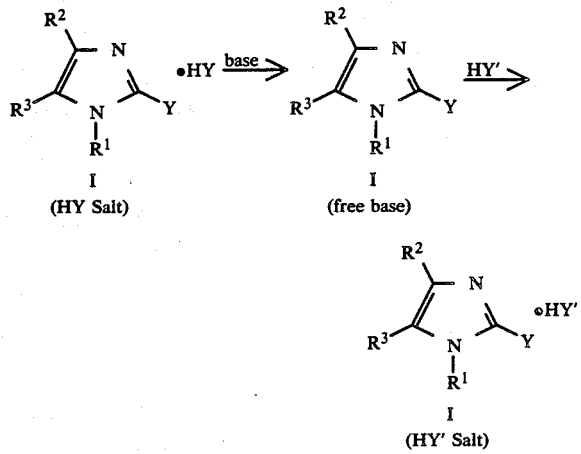

Alternatively, compounds of Formula I can be prepared by treating a 1-substituted-4,5-disubstituted imidazole (IIa) with a strong base such as n-butyllithium at about −78° C. to generate the anion at the 2-position, and then treating the anion with a source of "positive halogen" such as chlorine, bromine, dimethylsulfamoyl chloride or perchloryl fluoride at about 0° to −78°.

Equation 3

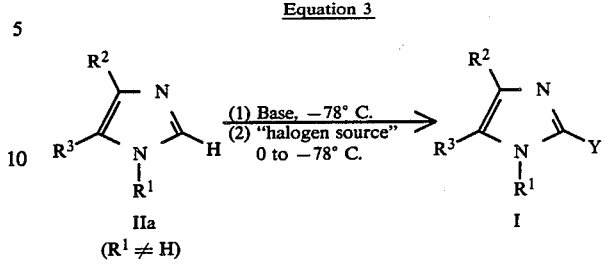

($R^1 \neq H$)

Compounds IIa where $R^1$ is methyl or 1-ethoxyethyl can be prepared from Compounds II where $R^1=H$ by base treatment and methylation, or by acid-catalyzed reaction with ethyl vinyl ether, respectively.

When Compounds (Ia) are prepared as illustrated in Equation 3, $R^1$ can not be hydrogen, and may or may not represent an acid labile N-protective group. When $R^1$ is such a protective group, e.g., 1-ethoxyethyl, Ia can be treated with an appropriate acid, removing the protective group $R^1$, to obtain Compounds I where $R^1=H$.

Equation 4

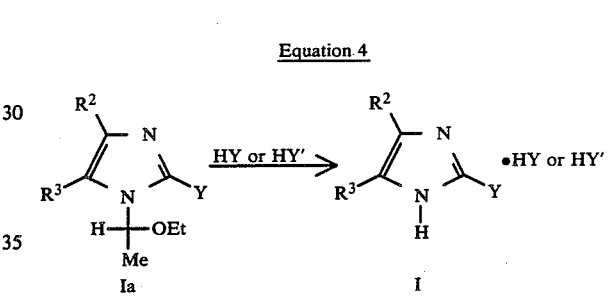

The reactions shown in Equations 2 and 4 are also useful methods of purifying the compounds of Formula I.

Compounds with $R^1=H$ can be converted to compounds where $R^1=CH_3$ by treatment with base and a suitable methylating agent such as methyl iodide.

The compounds of the invention and their synthesis are further illustrated by the following examples. All temperatures are in degrees Centigrade. Solvent ratios for thin-layer chromatography (tlc) are by volume.

The compounds made according to the procedures illustrated in Examples 1 to 9 are listed in Table I.

TABLE I

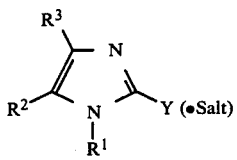

| Ex. | $R^1$ | $R^2$ | $R^3$ | Y | Salt, if any | m.p. | % Yield |
|---|---|---|---|---|---|---|---|
| 1 | H | 4-FC$_6$H$_4$ | 4-FC$_6$H$_4$ | Br | •HBr | 270–272 | 90 |
| 2 | H | 4-MeOC$_6$H$_4$ | 4-MeOC$_6$H$_4$ | Br | •HBr | 158–161 (dec) | 81 |
| 3 | H | 4-ClC$_6$H$_4$ | 4-ClC$_6$H$_4$ | Br | •HBr | 300 (dec) | 84 |
| 4 | H | 4-MeSC$_6$H$_4$ | 4-MeSC$_6$H$_4$ | Br | •HBr | 118 (dec) | 90 |
| 5 | H | 4-MeOC$_6$H$_4$ | 4-MeOC$_6$H$_4$ | Cl | •HCl | 129–132 | 100 |
| 6 | Me | 4-MeOC$_6$H$_4$ | 4-MeOC$_6$H$_4$ | Cl | — | 132–133 | 92 |
| 7 | —CH(OEt)Me | 4-MeOC$_6$H$_4$ | 4-MeOC$_6$H$_4$ | Cl | — | 118–120 | 50 |

EXAMPLE 1

2-Bromo-4,5-bis(4-fluorophenyl)-1H-imidazole, Hydrobromide

A suspension of 4,5-bis(4-fluorophenyl)-1H-imidazole (25.6 g, 0.1 mol) in chloroform (100 ml) was cooled in an ice bath and treated dropwise with bromine (16.0 g, 0.1 mol) in 50 ml of chloroform. The mixture was stirred in the ice bath for one hour and then at room temperature until no starting material was evidenced by tlc (toluene-ethyl acetate, 6:4). The reaction mixture was filtered and the resulting solid was washed with diethyl ether and dried in vacuo to yield 37.4 g (90%) of the title compound, m.p. 270°–272°.

Anal. Calcd. for $C_{15}H_9BrF_2N_2 \cdot HBr$: C, 43.30; H, 2.42; N, 6.73. Found: C, 43.25; H, 2.40; N, 6.70.

EXAMPLE 2

2-Bromo-4,5-bis(4-methoxyphenyl)-1H-imidazole, Hydrobromide

By substituting 4,5-bis(4-methoxyphenyl)-1H-imidazole in the procedure of Example 1, the title compound was obtained in 81% yield; m.p. 158°–161°.

EXAMPLE 3

2-Bromo-4,5-bis(4-chlorophenyl)-1H-imidazole, Hydrobromide

By substituting 4,5-bis(4-chlorophenyl)-1H-imidazole in the procedure of Example 1, the title compound was obtained in 84% yield, m.p. 300° (dec.).

EXAMPLE 4

2-Bromo-4,5-bis(4-methylthiophenyl)-1H-imidazole, Hydrobromide

By substituting 4,5-bis(4-methylthiophenyl)-1H-imidazole in the procedure of Example 1, the title compound was prepared in 90% yield, m.p. 118° (dec.).

EXAMPLE 5

2-Chloro-4,5-bis(4-methoxyphenyl)-1H-imidazole, Hydrochloride

A suspension of 4,5-bis(4-methoxyphenyl)-1H-imidazole (10.0 g, 0.036 mol) in 200 ml of carbon tetrachloride was treated with chlorine until no starting material was evidenced by tlc (chloroform-methanol-acetic acid, 17:1:2). The resulting solid was collected by filtration, washed with carbon tetrachloride, and dried in vacuo to yield 12.5 g (100%) of the title compound, m.p. 129°–132° (dec.).

EXAMPLE 6

2-Chloro-4,5-bis(4-methoxyphenyl)-1-methyl-1H-imidazole

A mixture of 4,5-bis(4-methoxyphenyl)-1-methyl-1H-imidazole (10.0 g, 0.034 mol) and N, N, N',N'-tetramethylethylenediamine (three equivalents) in 75 ml of dry tetrahydrofuran was cooled to −78° and treated with n-butyllithium (1.1 equivalents). The mixture was stirred at −78° under nitrogen for one hour and treated with dimethylsulfamoyl chloride (5.5 g, 0.038 mol). The mixture was stirred at −78° for 30 minutes and then overnight at room temperature. The reaction mixture was concentrated in vacuo, and the residue triturated with 10% citric acid. The resulting solid was collected by filtration, washed with water, and dried in vacuo to yield 10.3 g (92%) of the title compound, homogenous by tlc (toluene-ethyl acetate, 6:4; Rf=0.56), m.p. 132°–133°.

Anal. Calcd. for $C_{18}H_{17}ClN_2O_2$: C, 65.75; H, 5.21; N, 8.52. Found: C, 65.8; H, 5.3; N, 8.5.

EXAMPLE 7

2-Chloro-1-(1-ethoxyethyl)-4,5-bis(4-methoxyphenyl)-1H-imidazole

By substituting 1-(1-ethoxyethyl)-4,5-bis(4-methoxyphenyl)-1H-imidazole in the procedure of Example 6, the title compound was obtained in 50% yield after chromatography, m.p. 118°–120°.

Anal. Calcd. for $C_{21}H_{23}ClN_2O_3$: C, 65.19; H, 5.99; N, 7.24. Found: C, 65.5; H, 6.1; N, 7.1.

By using the methods described in the preceding examples, other compounds of Formula I can be prepared. Examples of such compounds are listed in Table II.

TABLE II

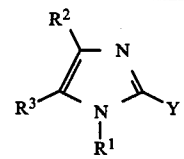

| Ex. | $R^3$ | $R^2$ | $R^1$ | Y | Salt |
|---|---|---|---|---|---|
| 10 | $4\text{-BrC}_6H_4$ | $4\text{-BrC}_6H_4$ | H | Br | — |
| 11 | $4\text{-BrC}_6H_4$ | $4\text{-BrC}_6H_4$ | H | Br | •HBr |
| 12 | $4\text{-BrC}_6H_4$ | $4\text{-BrC}_6H_4$ | MeCHOEt | Br | — |
| 13 | $4\text{-BrC}_6H_4$ | $4\text{-BrC}_6H_4$ | H | Cl | — |
| 14 | $4\text{-BrC}_6H_4$ | $4\text{-BrC}_6H_4$ | H | Cl | •HCl |
| 15 | $4\text{-BrC}_6H_4$ | $4\text{-BrC}_6H_4$ | MeCHOEt | Cl | — |
| 16 | $4\text{-BrC}_6H_4$ | $4\text{-BrC}_6H_4$ | H | F | — |
| 17 | $4\text{-BrC}_6H_4$ | $4\text{-BrC}_6H_4$ | H | F | •HCl |
| 18 | $4\text{-BrC}_6H_4$ | $4\text{-BrC}_6H_4$ | MeCHOEt | F | — |
| 19 | $4\text{-MeOC}_6H_4$ | $4\text{-MeOC}_6H_4$ | H | F | — |
| 20 | $4\text{-MeOC}_6H_4$ | $4\text{-MeOC}_6H_4$ | H | F | •HCl |
| 21 | $4\text{-MeOC}_6H_4$ | $4\text{-MeOC}_6H_4$ | Me | F | — |
| 22 | $4\text{-MeOC}_6H_4$ | $4\text{-MeOC}_6H_4$ | MeCHOEt | F | — |
| 23 | $4\text{-FC}_6H_4$ | $4\text{-FC}_6H_4$ | H | F | — |
| 24 | $4\text{-FC}_6H_4$ | $4\text{-FC}_6H_4$ | H | F | •HCl |
| 25 | $4\text{-FC}_6H_4$ | $4\text{-FC}_6H_4$ | MeCHOEt | F | — |
| 26 | $4\text{-ClC}_6H_4$ | $4\text{-ClC}_6H_4$ | H | F | — |
| 27 | $4\text{-ClC}_6H_4$ | $4\text{-ClC}_6H_4$ | H | F | •HCl |
| 28 | $4\text{-ClC}_6H_4$ | $4\text{-ClC}_6H_4$ | MeCHOEt | F | — |
| 29 | $4\text{-MeSC}_6H_4$ | $4\text{-MeSC}_6H_4$ | H | F | — |
| 30 | $4\text{-MeSC}_6H_4$ | $4\text{-MeSC}_6H_4$ | H | F | •HCl |
| 31 | $4\text{-MeSO}_2C_6H_4$ | $4\text{-MeSO}_2C_6H_4$ | MeCHOEt | F | — |
| 32 | $4\text{-FC}_6H_4$ | 3-pyridyl | H | Br | — |
| 33 | 2-pyridyl | $4\text{-FC}_6H_4$ | H | Cl | — |
| 34 | 2-pyridyl | $4\text{-FC}_6H_4$ | H | Br | — |
| 35 | $4\text{-ClC}_6H_4$ | $4\text{-C}_2H_5OC_6H_4$ | H | Br | — |
| 36 | $4\text{-ClC}_6H_4$ | $4\text{-C}_2H_5SC_6H_4$ | H | Br | — |
| 37 | $4\text{-FC}_6H_4$ | $4\text{-CH}_3S(O)C_6H_4$ | H | Br | — |

DOSAGE FORMS

The antiinflammatory agents of this invention can be administered to treat inflammation by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U,S. P., and 0.025 milliliters of vanillin.

Injectable

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

Use

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, Vol. 32, No. 2, 1973 "Models Used for the Study and Therapy of Rheumatoid Arthritis'-'—Symposium of the American Society for Pharmacology and Experimental Therapeutics —states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\begin{array}{c}\text{Arthritic Control}\\\text{Mean Paw Volume (ml)}\end{array} - \begin{array}{c}\text{Treatment Group}\\\text{Mean Paw Volume (ml)}\end{array}}{\begin{array}{c}\text{Arthritic Control}\\\text{Mean Paw Volume (ml)}\end{array} - \begin{array}{c}\text{Non-Arthritic Control}\\\text{Mean Paw Volume (ml)}\end{array}} \times 100 =$$

% Decrease from Control Mean Paw Volume.

Dose-response regression lines of the percent decrease are plotted on semi-log paper by visual fit and the ED50% decrease from control paw volume (effective dose at which a 50% decrease from control paw volume is observed) is determined by inspection. Data for some of the compounds in this invention are summarized in Table III.

Compounds from this series were also compared to indomethacin, phenylbutazone, ibuprofen, and aspirin.

TABLE III

| Example | Adjuvant Arthritis $ED_{50}$ (mg/kg) |
| --- | --- |
| 1 | 33% at 50* |
| 2 | 46% at 27* |
| 3 | 5.2 |
| 4 | 26% at 27* |
| 5 | 17% at 27* |
| 6 | 35% at 27* |
| 7 | 37% at 50* |
| Indomethacin | 0.3 |
| Phenylbutazone | 10 |
| Ibuprofen | 100 |
| Aspirin | 305 |

*Percent decrease from control paw volume at indicated daily dose in mg/kg.

What is claimed is:

1. A method of treating inflammation in a mammal which comprises administering to the mammal an effective antiinflammatory amount of at least one compound of the formula:

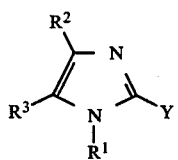

where
$R^1$ is H, methyl or 1-ethoxyethyl;
$R^2$ is pyridyl or

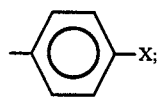

$R^3$ is pyridyl or

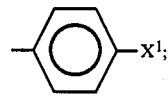

X and $X^1$ are independently F, Cl, Br, —$OR^4$ or $R^4S(O)_n$—;
$R^4$ is methyl or ethyl;
n is 0, 1 or 2; and
Y is F, Cl or Br;
provided that,
(a) when $R^1$ is methyl, then $R^2$ and $R^3$ are both 4-methoxyphenyl; and
(b) when $R^1$ is H, Y is Br and $R^2$ is 4-fluorophenyl, then $R^3$ is other than 4-methoxyphenyl; and
(c) when $R^1$ is H and $R^2$ and $R^3$ are 4-fluorophenyl, then Y is other than Cl;
or a pharmaceutically suitable acid addition salt thereof.

2. The method of claim 1 wherein $R^1$ is H.
3. The method of claim 1 wherein Y is Cl or Br.
4. The method of claim 1 wherein $R_2$ and $R_3$ are

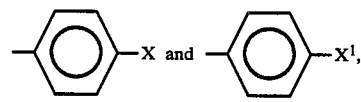

respectively, and X and $X^1$ are independently F, Cl, $OCH_3$ or $SCH_3$.

5. The method of claim 1 wherein $R^1$ is H;
Y is Cl or Br;
$R^2$ is

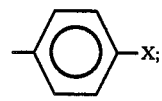

$R^3$ is

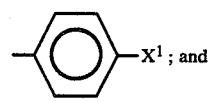

X and $X^1$ are independently F, Cl, $OCH_3$ or $SCH_3$.

6. The method of claim 1 wherein the compound is an acid addition salt of 2-bromo-4,5-bis(4-chlorophenyl)-1H-imidazole.

7. The method of claim 1 wherein the compound is 2-bromo-4,5-bis(4-chlorophenyl)-1H-imidazole, hydrobromide.

* * * * *